United States Patent
Fu et al.

(10) Patent No.: US 10,252,999 B2
(45) Date of Patent: Apr. 9, 2019

(54) PROCESS FOR PREPARING ALKYL ESTERS OF 4-(5-(BIS(2-HYDROXYETHYL)AMINO-1-METHYL-1H-BENZO[D]IMIDAZOL-2-YL)BUTYRIC ACID

(71) Applicant: Johnson Matthey Public Limited Company, London (GB)

(72) Inventors: Xing Fu, Acton, MA (US); Saroop Singh Matharu, Devens, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/844,889

(22) Filed: Dec. 18, 2017

(65) Prior Publication Data

US 2018/0105499 A1 Apr. 19, 2018

Related U.S. Application Data

(62) Division of application No. 14/209,147, filed on Mar. 13, 2014, now abandoned.

(60) Provisional application No. 61/790,386, filed on Mar. 15, 2013.

(51) Int. Cl.
C07D 235/16 (2006.01)
(52) U.S. Cl.
CPC .................................. *C07D 235/16* (2013.01)
(58) Field of Classification Search
CPC ................................................... C07D 235/16
See application file for complete search history.

(56) References Cited

U.S. PATENT DOCUMENTS

| | | |
|---|---|---|
| 2013/0184471 A1 | 7/2013 | Schickaneder et al. |
| 2013/0217888 A1 | 8/2013 | Shrawat et al. |
| 2013/0317234 A1 | 11/2013 | Pullagurla et al. |
| 2014/0031560 A1 | 1/2014 | Frey et al. |

FOREIGN PATENT DOCUMENTS

| | | |
|---|---|---|
| EP | 1724262 A1 | 11/2006 |
| WO | WO-2010144675 A1 | 12/2010 |
| WO | WO-2011079193 A2 | 6/2011 |
| WO | WO-2012007966 A2 | 1/2012 |
| WO | WO-2012059935 A1 | 5/2012 |
| WO | WO-2012176214 A2 | 12/2012 |
| WO | WO-2013046223 A1 | 4/2013 |
| WO | WO-2013150020 A1 | 10/2013 |

OTHER PUBLICATIONS

Gao, et al., "Synthesis of Bendamustine", Chinese Journal of New Drugs 2007 (16)23 pp. 1960, 1961, 1970 with English Abstract.
Gennari, et al., "Acceleration of Hemiacetal Cleavage through Hydrogen Bonding: A New Synthetic Catalyst with Balanced Conformational Flexibility and Preorganization", J. Org. Chem. 1991 (56) pp. 3201-3203.
Kabadoina, et al. Document No. 155:123408; retrieved from CAPLUS; Jun. 30, 2011.
Ozegowski, et al., "gamma-[1-methyl-5-bis-(beta-chloraethyl) amino benzimidazoly1-(2)]—butyric acid hydrochloride, a new cytostatic drug from the series of the benzimidazole-mustards", Zbl. Pharm. 1971 (110) 10 pp. 1013-1020 with English translation.
Pullagurla, et al. Document No. 156:175274, retrieved from CAPLUS; Jan. 19, 2012.
Stark, et al.; "Synthesis and Evaluation of Novel Spermidine Derivatives as Targeted Cancer Chemotherapeutic Agents"; J. Med. Chem. 1992 (35) pp. 4264-4269.
Tao, et al.; "Structure-Based Design, Synthesis, and Biological Evaluation of Potent and Selective Macrocyclic Checkpoint Kinase 1 Inhibitors"; J. Med. Chem. 2007 (50) pp. 1514-1527.
Werner, et al. Document No. 107:83787, retrieved from CAPLUS; 1987.
Wolfe, et al., "Convergent Functional Groups: Catalysis of Hemiacetal Cleavage in a Synthetic Molecular Cleft", J. Am. Chem. Soc. 1988 (110) pp. 983-984.

*Primary Examiner* — Shawquia Jackson
(74) *Attorney, Agent, or Firm* — Raymond S. Parker

(57) ABSTRACT

An alkyl ester of 4-(5-(bis(2-hydroxyethyl)amino)-1-methyl-1H-benzo[d]imidazol-2-yl)butyric acid, such as ethyl 4-(5-(bis(2-hydroxyethyl)amino)-1-methyl-1H-benzo[d]imidazol-2-yl)butanoate, is obtained by reacting an alkyl ester of 4-(5-amino-1-methyl-1H-benzo[d]imidazol-2-yl)butyric acid with 2-hydroxyacetaldehyde under reducing conditions.

10 Claims, 1 Drawing Sheet

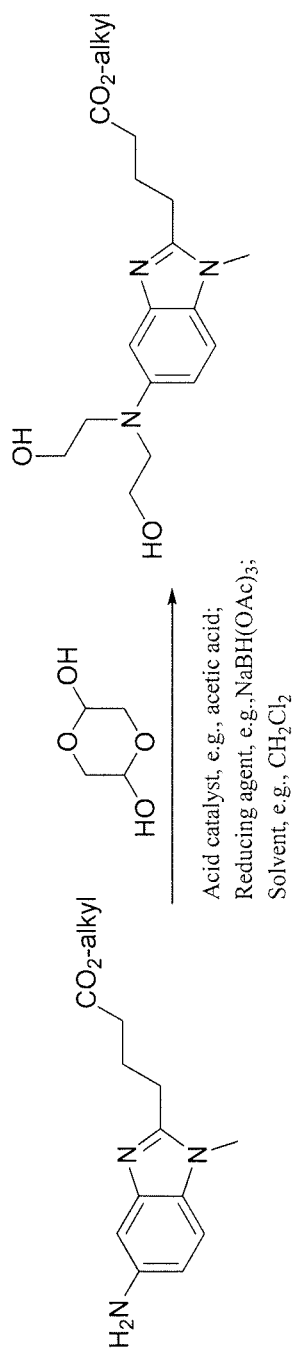

PROCESS FOR PREPARING ALKYL ESTERS OF 4-(5-(BIS(2-HYDROXYETHYL)AMINO-1-METHYL-1H-BENZO[D]IMIDAZOL-2-YL) BUTYRIC ACID

CROSS-REFERENCE TO RELATED APPLICATIONS

This application is a divisional of U.S. patent application Ser. No. 14/209,147, filed Mar. 13, 2014 and claims priority to U.S. Provisional Patent Application No. 61/790,386, filed Mar. 15, 2013, the disclosures of which are incorporated herein by reference in their entireties for all purposes.

FIELD OF THE INVENTION

The invention pertains to synthetic methods for converting an alkyl ester of 4-(5-amino-1-methyl-1H-benzo[d]imidazol-2-yl)butyric acid (such as ethyl 4-(5-amino-1-methyl-1H-benzo[d]imidazol-2-yl)butanoate, CAS No. 3543-73-5) to the corresponding alkyl ester of 4-(5-(bis(2-hydroxyethyl)amino)-1-methyl-1H-benzo[d]imidazol-2-yl)butyric acid (e.g., ethyl 4-(5-(bis(2-hydroxyethyl)amino)-1-methyl-1H-benzo[d]imidazol-2-yl)butanoate, CAS No. 3543-74-6), which are useful intermediates in the production of bendamustine.

BACKGROUND OF THE INVENTION

Bendamustine is a nitrogen mustard used in the treatment of chronic lymphocytic leukemias and lymphomas and is also being studied for the treatment of sarcoma. It belongs to the family of drugs referred to as alkylating agents.

The synthesis of bendamustine hydrochloride monohydrate has been reported by Ozegowski and Krebs, *J. Praktische Chemie*, 4(20), 178-186 (1963) and by Gao et al., *Chinese Journal of New Drugs*, 16(23), 1960-1, 1970 (2007). The synthetic sequences described in these publications involve a step wherein ethyl 4-(5-amino-1-methyl-1H-benzo[d]imidazol-2-yl)butanoate is converted to ethyl 4-(5-(bis(2-hydroxyethyl)amino)-1-methyl-1H-benzo[d]imidazol-2-yl)butanoate by reaction of the former compound with two equivalents of ethylene oxide. However, this approach may lead to the generation of undesired side products such as those produced from further reaction of the terminal hydroxyl group(s) of the target compound with ethylene oxide. In other words, the ethyl 4-(5-(bis(2-hydroxyethyl)amino)-1-methyl-1H-benzo[d]imidazol-2-yl)butanoate may further react with additional ethylene oxide to introduce oligooxyethylene groups into the molecule. Additionally, although it is currently used in many industrial applications, ethylene oxide is recognized as a very hazardous substance. At room temperature, it is a flammable, carcinogenic, mutagenic, irritating and anesthetic gas with a misleadingly pleasant aroma. Its use in the routine large scale production of bendamustine would therefore pose serious safety and handling issues.

Accordingly, it would be desirable to develop alternative approaches for synthesizing alkyl esters of 4-(5-(bis(2-hydroxyethyl)amino)-1-methyl-1H-benzo[d]imidazol-2-yl) butyric acid, such as ethyl 4-(5-(bis(2-hydroxyethyl)amino)-1-methyl-1H-benzo[d]imidazol-2-yl)butanoate, which avoid the use of ethylene oxide as a reactant and which have reduced potential for the generation of by-products.

SUMMARY OF THE INVENTION

The present invention provides a process for synthesizing alkyl esters of 4-(5-(bis(2-hydroxyethyl)amino)-1-methyl-1H-benzo[d]imidazol-2-yl)butyric acid, intermediates useful for making the active pharmaceutical ingredient bendamustine, which avoids the use of ethylene oxide and which provides high yields of the desired products.

One aspect of the invention relates to a method of producing an alkyl ester of 4-(5-(bis(2-hydroxyethyl)amino)-1-methyl-1H-benzo[d]imidazol-2-yl)butyric acid, comprising a step of reacting an alkyl ester of 4-(5-amino-1-methyl-1H-benzo[d]imidazol-2-yl)butyric acid with 2-hydroxyacetaldehyde.

Another aspect of the invention furnishes a method of producing an alkyl ester of 4-(5-(bis(2-hydroxyethyl)amino)-1-methyl-1H-benzo[d]imidazol-2-yl)butyric acid, comprising a step of reacting an alkyl ester of 4-(5-amino-1-methyl-1H-benzo [d]imidazol-2-yl)butyric acid with glycolaldehyde dimer under acidic reducing conditions.

Yet another aspect of the invention provides a method of producing an alkyl ester of 4-(5-(bis(2-hydroxyethyl)amino)-1-methyl-1H-benzo[d]imidazol-2-yl)butyric acid, comprising a step of reacting an alkyl ester of 4-(5-amino-1-methyl-1H-benzo[d]imidazol-2-yl)butyric acid with glycolaldehyde dimer in a reaction medium comprising an organic solvent, a glycolaldehyde dimer dissociation catalyst (e.g., an acid such as acetic acid) and a reducing agent (e.g., a borohydride reducing agent such as sodium triacetoxyborohydride).

A further aspect of the present invention provides an alkyl ester of 4-(5-(bis(2-hydroxyethyl)amino)-1-methyl-1H-benzo[d]imidazol-2-yl)butyric acid (e.g., ethyl 4-(5-(bis(2-hydroxyethyl)amino)-1-methyl-1H-benzo[d]imidazol-2-yl) butanoate) which is substantially free of by-products containing oligooxyethylene groups. In other aspects of the invention, an alkyl ester of 4-(5-(bis(2-hydroxyethyl)amino)-1-methyl-1H-benzo[d]imidazol-2-yl)butyric acid (e.g., ethyl 4-(5-(bis(2-hydroxyethyl)amino)-1-methyl-1H-benzo[d]imidazol-2-yl)butanoate) is provided which is at least 93% pure, at least 95% pure, or at least 97.5% pure, as measured by HPLC area % analysis.

DESCRIPTION OF THE DRAWING

FIG. 1 shows an exemplary reaction scheme in accordance with one aspect of the invention.

DETAILED DESCRIPTION OF THE INVENTION

The present invention introduces a bis(2-hydroxyethyl) moiety onto the amine functional group of an alkyl ester of 4-(5-amino-1-methyl-1H-benzo[d]imidazol-2-yl)butyric acid (which may also be referred to as an "alkyl 4-(5-amino-1-methyl-1H-benzo[d]imidazol-2-yl)butanoate") by reacting the amine group with two equivalents of 2-hydroxyacetaldehyde ($HOCH_2CH=O$), followed by reduction of the imine/iminium species thus formed. The alkyl group present in the alkyl ester starting material (and thus also present in the alkyl ester product formed therefrom) may be any type of alkyl group known in the art including, for example, a C1 to C6 alkyl group (either straight chain or branched). Suitable alkyl groups include, without limitation, methyl, ethyl, n-propyl, isopropyl, n-butyl, sec-butyl, isobutyl, t-butyl and the like. The alkyl ester of 4-(5-amino-1-methyl-1H-benzo [d]imidazol-2-yl)butyric acid starting material may be prepared in accordance with any of the synthetic methods known in the art, including those described in Ozegowski and Krebs, *J. Praktische Chemie*, 4(20), 178-186 (1963) and in Gao et al., *Chinese Journal of New Drugs*, 16(23), 1960-1, 1970 (2007). The 2-hydroxyacetaldehyde (which is also referred to in the art as "glycolaldehyde") may be conveniently generated in situ from glycolaldehyde dimer, which is readily available from commercial sources. Glycolaldehyde dimer is a masked dimer of 2-hydroxyacetaldehyde, which dissociates to the monomer in the presence of a glycolaldehyde dimer dissociation catalyst. The glycolaldehyde dimer dissociation catalyst may be an acid or a combination of different acids. Suitable acid catalysts include, for example, carboxylic acids such as acetic acid, trifluoroacetic acid, formic acid, propionic acid, butyric acid, benzoic acid and glutaric acid as well as combinations of different acid catalysts. Other suitable glycolaldehyde dimer dissociation catalysts include 2-hydroxypyridine, for example. In order to avoid a possible aldol condensation side reaction of 2-hydroxyacetaldehyde under acidic conditions, the glycolaldehyde dimer may be introduced in portions as the last reagent into the reaction mixture. For example, a one-pot reaction may be performed in a reaction mixture comprising an organic solvent such as dichloromethane (containing the alkyl ester of 4-(5-amino-1-methyl-1H-benzo[d]imidazol-2-yl)butyric acid starting material), an acid catalyst and a reducing agent, wherein the glycolaldehyde dimer is added incrementally (e.g., in portions) to the reaction mixture. Both the glycolaldehyde dimer and the reducing agent may be added incrementally to a mixture comprising the starting material, a glycolaldehyde dimer dissociation catalyst and an organic solvent. Portions of the reducing agent alternating with portions of the glycolaldehyde dimer may be added to such a mixture.

FIG. 1 illustrates a reaction scheme in accordance with one embodiment of the invention wherein an alkyl ester of 4-(5-amino-1-methyl-1H-benzo[d]imidazol-2-yl)butyric acid is reacted with glycolaldehyde dimer in the presence of a glycolaldehyde dimer dissociation catalyst, a reducing agent and organic solvent to yield an alkyl ester of 4-(5-(bis(2-hydroxyethyl)amino)-1-methyl-1H-benzo[d]imidazol-2-yl)butyric acid.

Typically, the reaction of the alkyl ester of 4-(5-amino-1-methyl-1H-benzo[d]imidazol-2-yl)butyric acid with the 2-hydroxyacetaldehyde and reducing agent may be carried out at temperatures of from about 0° C. to about 40° C., preferably from about 0° C. to about 25° C. Generally speaking, the molar ratio of 2-hydroxyacetaldehyde to alkyl ester of 4-(5-amino-1-methyl-1H-benzo[d]imidazol-2-yl) butyric acid is suitably about 2:1 or somewhat higher, e.g., about 2:1 to about 6:1 or preferably about 2:1 to about 4:1.

Any suitable reducing agent capable of reducing the initially formed imine/iminium species resulting from reaction of the alkyl ester of 4-(5-amino-1-methyl-1H-benzo[d] imidazol-2-yl)butyric acid with the 2-hydroxyacetaldehyde to the desired bis(hydroxyethyl)-functionalized product may be utilized. For example, the reducing agent may be a borohydride, such as sodium borohydride, sodium cyanoborohydride, sodium triacetoxyborohydride, alkyl and dialkyl cyanoborohydrides, potassium borohydride, zinc borohydride, and lithium tri-sec-butyl borohydride and combinations of different borohydrides. Borane and sodium dithionite may also be utilized as the reducing agent. In another embodiment of the invention, hydrogen ($H_2$) is used as the reducing agent, advantageously together with a catalyst. Generally speaking, a molar excess of reducing agent is employed, e.g., the molar ratio of reducing agent to the imine/iminium species may be from about 2:1 to about 6:1 or, advantageously, from about 4:1 to about 6:1.

The 2-hydroxyacetaldehyde reaction and the reduction step are generally carried out concurrently.

The desired product, the alkyl ester of 4-(5-(bis(2-hydroxyethyl)amino)-1-methyl-1H-benzo[d]imidazol-2-yl)butyric acid, may be isolated from the reaction mixture using any suitable combination of techniques known in the art, such as neutralization, filtration, extraction and/or recrystallization. For example, upon completion of reaction the reaction mixture obtained (containing a water immiscible organic solvent such as dichloromethane) may be neutralized with an aqueous solution of a base such as potassium bicarbonate. Following filtration, the organic and aqueous phases are separated and the aqueous phase washed one or more times with a water immiscible organic solvent. The organic extracts are combined, dried, and then stripped of solvent to provide the crude alkyl ester of 4-(5-(bis(2-hydroxyethyl)amino)-1-methyl-1H-benzo[d]imidazol-2-yl) butyric acid, which may be recrystallized from a suitable solvent such as ethyl acetate, isolated by filtration, and then dried to yield purified alkyl ester of 4-(5-(bis(2-hydroxyethyl)amino)-1-methyl-1H-benzo[d]imidazol-2-yl)butyric acid.

The purity of the alkyl 4-(5-(bis(2-hydroxyethyl)amino)-1-methyl-1H-benzo[d]imidazol-2-yl)butanoates obtained by practice of the present invention may be analyzed by High Performance Liquid Chromatography (HPLC). In particular, the following HPLC method is suitable:

Chromatographic Conditions:
Column: Waters Sunfire® C18, 5 μm, 150×4.6 mm
Mobile Phase:
  Solvent A: 0.2% Trifluoroacetic acid in water
  Solvent B: 0.2% Trifluoroacetic acid in acetonitrile
Gradient:

| Time (Minutes) | % A | % B |
| --- | --- | --- |
| 0.0 | 95 | 5 |
| 2.0 | 95 | 5 |
| 25.0 | 40 | 60 |
| 27.0 | 0 | 100 |
| 30.0 | 0 | 100 |
| 30.1 | 95 | 5 |
| 37.0 | 95 | 5 |

Detection: UV 254 nm
Sample Diluent: 0.5% Trifluoroacetic acid in 50:50 Acetonitrile/Water
Injection Volume: 5 μL
Flow Rate: 1.0 mL/min The HPLC area % of a particular component is the percentage represented by the area under the peak for that component of the total area under the curve of an HPLC trace for an analyzed sample.

The alkyl ester of 4-(5-(bis(2-hydroxyethyl)amino)-1-methyl-1H-benzo[d]imidazol-2-yl)butyric acid may be free or substantially free of by-products containing oligooxyethylene groups. For example, an alkyl ester of 4-(5-(bis(2-hydroxyethyl)amino)-1-methyl-1H-benzo[d]imidazol-2-yl) butyric acid may be produced in accordance with the present invention having less than 1%, less than 0.5%, or less than 0.1% of by-products containing oligooxyethylene groups, as determined by HPLC area % analysis.

In other embodiments of the invention, an alkyl ester of 4-(5-(bis(2-hydroxyethyl)amino)-1-methyl-1H-benzo[d] imidazol-2-yl)butyric acid, such as the ethyl ester, is obtained having a purity, as determined by HPLC area % analysis, of at least 93%, at least 95%, or at least 97.5%.

Although the invention is illustrated and described herein with reference to specific embodiments, the invention is not intended to be limited to the details shown. Rather, various modifications may be made in the details within the scope and range of equivalents of the claims and without departing from the invention.

EXAMPLE

An ethyl 4-(5-amino-1-methyl-1H-benzo[d]imidazol-2-yl)butanoate starting material (385 g) is charged under inert atmosphere to a suitably sized reactor followed by dichloromethane (4.8 L) and acetic acid (126 mL, 1.50 equivalents). The stirred solution is cooled to 5±5° C.

Sodium triacetoxyborohydride (1405.1 g, 4.50 equiv) is dispensed as five equal portions (281.0 g each) into five separate containers and likewise glycolaldehyde dimer (212.0 g, 1.20 equivalents) is dispensed as five equal portions (42.5 g each) into five separate containers. The first portion of sodium triacetoxyborohydride is charged in portions while maintaining the reaction temperature at <25° C. followed by the first portion of glycolaldehyde dimer while also maintaining the reaction temperature at <25° C. The reaction mixture is stirred for a minimum of 10 minutes and then the second portion of sodium triacetoxyborohydride is charged in a similar manner followed by the second portion of glycolaldehyde dimer while maintaining the reaction temperature at <25° C. The alternate additions of sodium triacetoxyborohydride and glycolaldehyde dimer portions are then continued until the addition of the two reagents is complete. The batch is allowed to warm to 20±5° C. and stirred for 12±6 h. The reaction is monitored for completion by HPLC analysis.

On completion the reaction mixture is cooled to 8±3° C. and a 20% w/w solution of potassium bicarbonate is charged cautiously in portions such that gas evolution does not become vigorous. The batch is then heated at 35±3° C. for 4.0±0.5 h, then cooled to 20±5° C. and neutralized, if necessary, to pH>7 by addition of 20% w/w solution of potassium bicarbonate and then filtered through Celite® filter aid. The lower organic layer is separated and the aqueous layer is extracted twice with dichloromethane (2×385 mL). The combined organic extract is dried over sodium sulfate (186 g) and the solvent removed under reduced pressure at 25±5° C. until no solvent distills over. Ethyl acetate (600 mL) is added and the evaporation of solvent under reduced pressure at 25±5° C. continued until no solvent distills over. More ethyl acetate (1350 mL) is then added to induce crystallization and the mixture transferred into a reactor using ethyl acetate (300 mL) as a rinse. The batch is stirred at 20±5° C. for 4 to 18 h and then the solid product [ethyl 4-(5-(bis(2-hydroxyethyl)amino)-1-methyl-1H-benzo[d]imidazol-2-yl)butanoate] is filtered, washed with ethyl acetate (500 mL) and dried under high vacuum at 30±5° C. to constant weight.

A second crop of the product can be obtained by evaporation of solvent from the filtrate under reduced pressure at 25±5° C. The residue is then dissolved in dichloromethane (2.0 mL/g of starting material), and the solution washed with 20% w/w solution of potassium bicarbonate until the pH of the aqueous layer is >7. The organic layer is then separated and dried over sodium sulfate. The sodium sulfate is filtered, the filter cake washed with dichloromethane and the solvent removed under reduced pressure. Ethyl acetate is then added to induce crystallization. The batch is stirred at 20±5° C. for a minimum of 0.5 h and then the solid product filtered, washed with ethyl acetate and dried under high vacuum at 30±5° C. to constant weight.

The ethyl 4-(5-(bis(2-hydroxyethyl)amino)-1-methyl-1H-benzo[d]imidazol-2-yl)butanoate product is obtained as a white to pinkish white solid in 70% to 95% yield.

What is claimed is:

1. A method of producing an alkyl ester of 4-(5-(bis(2-hydroxyethyl)amino)-1-methyl-1H-benzo[d]imidazol-2-yl) butyric acid, comprising reacting an alkyl ester of 4-(5-amino-1-methyl-1H-benzo[d]imidazol-2-yl)butyric acid with glycolaldehyde dimer under acidic reducing conditions.

2. A method of producing an alkyl ester of 4-(5-(bis(2-hydroxyethyl)amino)-1-methyl-1H-benzo[d]imidazol-2-yl) butyric acid, comprising reacting an alkyl ester of 4-(5-amino-1-methyl-1H-benzo[d]imidazol-2-yl)butyric acid with glycolaldehyde dimer in a reaction medium comprised of organic solvent, a glycolaldehyde dimer dissociation catalyst and a reducing agent, wherein the glycolaldehyde dimer dissociation catalyst is selected from the group consisting of 2-hydroxypyridine and an acid, wherein the acid is selected from the group consisting of acetic acid, trifluoroacetic acid, formic acid, propionic acid, butyric acid, benzoic acid, and glutaric acid, and a combination of the acids.

3. The method of claim 2, wherein the solvent is dichloromethane.

4. The method of claim 2, wherein the glycolaldehyde dimer dissociation catalyst is an acid, wherein the acid is selected from the group consisting of acetic acid, trifluoroacetic acid, formic acid, propionic acid, butyric acid, benzoic acid, and glutaric acid, and a combination of the acids.

5. The method of claim 2, wherein the reducing agent is a borohydride or combination of borohydrides.

6. The method of claim 2, wherein the reducing agent is sodium cyanoborohydride or sodium triacetoxyborohydride.

7. The method of claim 2, wherein the reaction is carried out by the glycolaldehyde dimer being added incrementally to the reaction medium.

8. The method of claim 2, wherein the reaction is carried out by the glycolaldehyde dimer and the reducing agent being added incrementally to the reaction medium.

9. The method of claim 2, wherein the alkyl ester of 4-(5-amino-1-methyl-1H-benzo[d]imidazol-2-yl)butyric acid is a C1 to C6 branched or straight chain alkyl ester of 4-(5-amino-1-methyl-1H-benzo[d]imidazol-2-yl)butyric acid.

10. The method of claim 2, wherein the alkyl ester of 4-(5-amino-1-methyl-1H-benzo[d]imidazol-2-yl)butyric acid is an ethyl or isopropyl ester of 4-(5-amino-1-methyl-1H-benzo[d]imidazol-2-yl)butyric acid.

* * * * *